US008193499B2

(12) United States Patent
Nagao et al.

(10) Patent No.: US 8,193,499 B2
(45) Date of Patent: Jun. 5, 2012

(54) SURFACE ENHANCED INFRARED ABSORPTION SENSOR AND METHOD FOR PRODUCING THE SAME

(75) Inventors: Tadaaki Nagao, Tsukuba (JP); Dominik Enders, Tsukuba (JP); Tomonobu Nakayama, Tsukuba (JP); Masakazu Aono, Tsukuba (JP)

(73) Assignee: National Institute for Materials Science, Ibaraki (JP)

( * ) Notice: Subject to any disclaimer, the term of this patent is extended or adjusted under 35 U.S.C. 154(b) by 193 days.

(21) Appl. No.: 12/676,723

(22) PCT Filed: Sep. 5, 2008

(86) PCT No.: PCT/JP2008/066107
§ 371 (c)(1),
(2), (4) Date: May 11, 2010

(87) PCT Pub. No.: WO2009/031662
PCT Pub. Date: Mar. 12, 2009

(65) Prior Publication Data
US 2010/0239821 A1    Sep. 23, 2010

(30) Foreign Application Priority Data
Sep. 7, 2007   (JP) ................................. 2007-233049

(51) Int. Cl.
*G01J 5/58* (2006.01)
(52) U.S. Cl. .................................................. 250/338.1
(58) Field of Classification Search ............... 250/338.1, 250/338.4, 339.01
See application file for complete search history.

(56) References Cited

OTHER PUBLICATIONS

International Search Report issued Dec. 9, 2008 in corresponding International Application No. PCT/JP2008/066107.
D. C. Bradford et al., "Infrared Ellipsometry of Self-Assembled Octadecylmercaptan on Gold Films and Nanoislands: Effects of Thickness and Morphology of the Gold Layer", Journal of Physical Chemistry B, Nov. 11, 2004, vol. 108, No. 45, pp. 17523-17530.
Dominik Enders et al., "Surface enhanced infrared absorption on Au nanoparticle films deposited on $SiO_2$/Si for optical biosensing: Dectection of the antibody-antigen reaction", Surface Science, vol. 600, No. 23, Dec. 1, 2006, pp. L305-L308.
Dominik Enders et al., "Two-Step Desorption Process of Au Nanoparticles in $D_2O$ Suspension on Amino-Terminated $SiO_2$/Si Substrate Induced by Small Thiol Molecules", Japanese Journal of Applied Physics, Prat 1. Regular papers, Short Notes & Review papers, May 15, 2007, vol. 46, No. 5, pp. 3020-3023.

*Primary Examiner* — Mark R Gaworecki
(74) *Attorney, Agent, or Firm* — Wenderoth, Lind & Ponack, L.L.P.

(57) ABSTRACT

The method for producing a surface enhanced infrared absorption sensor of the invention is characterized by: adsorbing metallic nanoparticles dispersed in a solution on a surface of a substrate, or allowing the adsorbed metallic nanoparticles to be grown in a solution, thereby forming a film; applying infrared light to the substrate from the side thereof opposite to the side on which the metallic nano-thin film is disposed; detecting evanescent waves exuding from the substrate; and regulating a surface enhanced infrared adsorption activity while monitoring surface enhanced infrared adsorption signals in situ, whereby the metallic nano-thin film is grown in the form of flat and discontinuous islands. According to the method, there is provided a production technique for a surface enhanced infrared absorption (SEIRA) sensor having a higher sensitivity and more excellent in the reproducibility.

3 Claims, 12 Drawing Sheets

(a)

Detection of Organic Molecules in Solution (b)

Detection of Antigen-Antibody Reaction

Colloidal suspension

SURFACE ENHANCED INFRARED ABSORPTION SENSOR AND METHOD FOR PRODUCING THE SAME

TECHNICAL FIELD

The present invention relates to a surface enhanced infrared absorption sensor with metallic nano-thin films adsorbed by a substrate, and to a method for producing the same.

BACKGROUND ART

As shown in Non-Patent Reference 1, the effect of surface enhanced infrared absorption (hereinafter this may be referred to as SEIRA) is actively studied these days as a phenomenon applicable to high-sensitivity and simple chemical sensors/biosensors. SEIRA sensors directly monitor the frequency of molecular oscillation, differing from dielectric sensors such as surface plasmon sensors, or resistance-detecting gas sensors, etc. Therefore, they exhibit their power in detecting the components of molecular species and in monitoring states/environments, for example, in detecting the components of biological molecules/polymers and the like and monitoring their state changes, or in monitoring the reaction process of chemical species on the surface of electrodes in fuel cells, etc. Metallic films comprising fine particles and metallic films having a rough surface morphology have a high SEIRA activity, and therefore, there are known many cases of using nano-thin films of such metallic films grown on a semiconductor/insulator substrate as sensor materials.

Heretofore, for producing SEIRA-active sensor materials, widely used is a method of forming a continuous film island-like grown on a semiconductor substrate through vacuum vapor deposition. However, the production method requires an expensive vacuum apparatus, and the sensor film produced in such a vacuum apparatus must be once taken out of the apparatus and checked one by one immediately after its production according to an infrared absorption method, and therefore the method detracts from efficient control of the SEIRA activity of the sensor materials. Accordingly, a simpler and more inexpensive production method for SEIRA sensors is desired. In addition, the SEIRA sensors produced according to the vacuum vapor deposition method are not still satisfactory in the sensitivity and the reproducibility thereof; and it is desired to realize SEIRA sensors having a higher sensitivity and more excellent in the reproducibility.

Regarding the technology relating to the SEIRA effect, Non-Patent Reference 2 discloses a report of studies relating to the kinetics and the molecular process in adsorption/desorption of fine particle film in solution using a SEIRA method; Non-Patent Reference 3 discloses a first report relating to monitoring of adsorption/desorption of metallic fine particles in solution using a SEIRA method; and Non-Patent Reference 4 discloses a report of studies relating to the molecular process in desorption of fine particle film in solution using a SEIRA method.

[Non-Patent Reference 1] M. Osawa, Bull. Chem. Soc. Jpn. 70, 2681-2880 (1997)
[Non-Patent Reference 2] D. Enders, T. Nagao, T. Nakayama, and M. Aono, Langmuir 23, 6119 (2007)
[Non-Patent Reference 3] D. Enders, T. Nagao, A. Pucci and T. Nakayama, Surf. Sci., 600, L71 (2006)
[Non-Patent Reference 4] D. Enders, T. Nagao, and T. Nakayama, Jpn. J. Appl. Phys. 46, 3020 (2007)

DISCLOSURE OF THE INVENTION

The present invention has been made in consideration of the prior-art situation as above, and its object is to provide a surface enhanced infrared absorption (SEIRA) sensor capable of being produced in a simpler and more inexpensive manner and having a higher sensitivity and excellent reproducibility, and to provide a method for producing the same.

To solve the above-mentioned problems, the invention first provides a surface enhanced infrared absorption sensor material with metallic nano-thin films adsorbed on a dielectric substrate, wherein the metallic nano-thin films are disposed on the substrate as flat and discontinuous islands having a two-dimensional filling factor of from 0.7 to less than 1, and the average gap between the adjacent islands is at most 7 nm.

Secondly, the invention provides a method for producing a surface enhanced infrared adsorption sensor with a metallic nano-thin film adsorbed on a dielectric substrate, characterized by: adsorbing metallic nanoparticles dispersed in a solution on a surface of a substrate, or allowing the adsorbed metallic nanoparticles to be grown at the substrate-solution interface, thereby forming a film; applying infrared light to the substrate from the side thereof opposite to the side on which the metallic nano-thin film is disposed; detecting the reflected bean and utilizing the evanescent waves exuding from the substrate for proving the optical properties of the metallic nano-thin films; and regulating a surface enhanced infrared adsorption activity while monitoring surface enhanced infrared adsorption signals in situ, whereby the metallic nano-thin film is grown in the form of flat and discontinuous islands.

Thirdly, there is provided a method for producing a surface enhanced infrared absorption sensor of the second invention, wherein the metallic nano-thin films are so formed on the substrate that they have a two-dimensional filling rate of from 0.7 to less than 1 and that the average gap between the adjacent islands is at most 7 nm.

Fourthly, there is provided a method for producing a surface enhanced infrared absorption sensor of the second or third invention, wherein the irradiation with infrared light is monitored according to an attenuated total reflectance method.

According to the invention, the above-mentioned technical means or method is employed, and therefore, there are provided a surface enhanced infrared absorption (SEIRA) sensor having a higher sensitivity and excellent in reproducibility in a simpler and more inexpensive manner, and a method for producing the same. In addition, according to the invention, there is provided a technique of producing a high-sensitivity SEIRA active film in a simple and rapid manner with good reproducibility, in which, while the active film is produced, its activity is in situ evaluated.

BEST MODE FOR CARRYING OUT THE INVENTION

Embodiments of the invention are described in detail hereinunder.

First, a surface enhanced infrared absorption (SEIRA) sensor material of an embodiment of the invention is described.

The SEIRA sensor material of this embodiment comprises metallic nano-thin films adsorbed by a dielectric substrate, in which the metallic nano-thin films are disposed on the substrate as flat and discontinuous islands having a two-dimensional filling rate of from 0.7 to less than 1, and the average gap between the adjacent islands is at most 7 nm.

Figure 1:
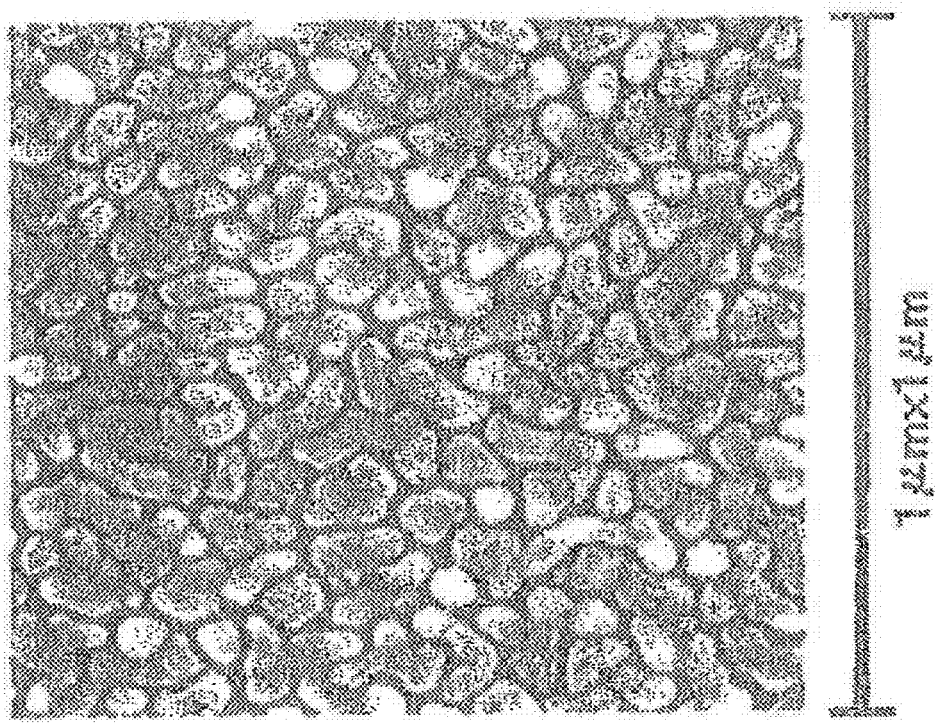
FIG. 1 is a view showing the appearance of metallic nano-thin films formed in a SEIRA material of the invention.

FIG. 1 shows the appearance of metallic nano-thin films formed in the SEIRA sensor material of this embodiment. This case is a scanning electron microscopic (SEM) image of metallic nano-thin films of Au formed on a silicon substrate having a native oxide film on its surface, according to the method mentioned below. It is known that metallic nano-thin films are disposed as a large number of islands spaced by a narrow gap from each other.

The SEIRA activity increases when the gap between the island-like metallic nano-thin films becomes narrower; and as is obvious from Examples given below, the gap is preferably at most 7 nm. The lower limit of the gap is 3 nm, which is the percolation threshold value just before the metallic nano-thin films begin to aggregate and the entire system begins to express electroconductivity. For high sensitivity, the size of the metallic nano-thin film is preferably from 50 to 200 nm or so on average. Also preferably, the two-dimensional filling factor is at least 0.7, and the upper limit thereof is a value of less than 1 with which the film loses discontinuity. "Two-dimensional filling rate" as referred to herein means the ratio of the total area of the metallic nano-thin films in a unit area (thin film-occupied area ratio), based on the overall area of 1 (one). Preferably, the individual metallic nano-thin films have a high degree of flatness; and in particular, the ratio of thickness-width of the film is preferably at most 0.2.

As the metallic nano-thin film in the SEIRA sensor material of the invention, usable are Ag, Cu, Pd, Pt, Fe and the like, in addition to Au. Also usable are oxides and semiconductors that can exhibit electroconductivity when doped or when modified to have a heterogeneous interface. As the dielectric substrate, usable are similar Fe, GaAs, ZnSe, alumina, $SrTiO_3$, $BaF_2$ and the like, in addition to Si of which the surface is coated with a native oxide film.

Figure 2:
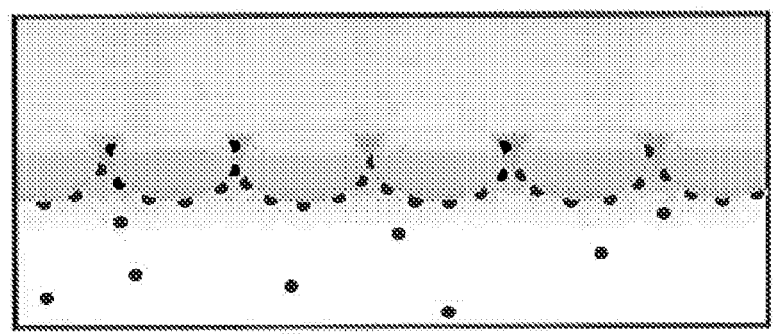
FIG. 2(a) is a view showing an application example of a SEIRA material of the invention to a chemical sensor.
FIG. 2(b) is a view showing an application example of a SEIRA material of the invention to a biosensor.
Figure 2:
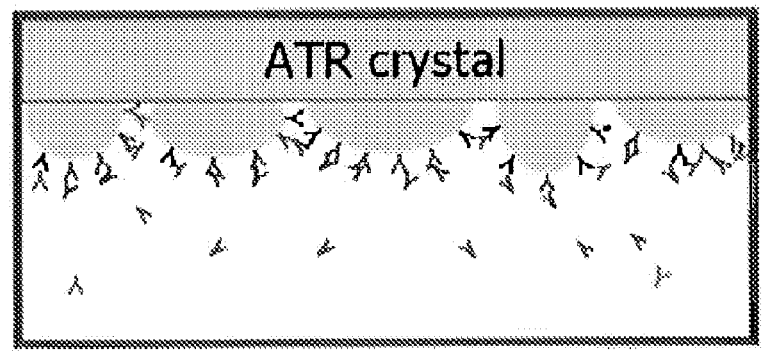

FIG. 2(*a*) shows an application example of a SEIRA sensor material of the invention to a chemical sensor; FIG. 2(*b*) shows an application example thereof to a biosensor.

Next described is a method for producing the SEIRA sensor material of an embodiment of the invention.

The method for producing a SEIRA sensor material of this embodiment is characterized by: adsorbing metallic nanoparticles dispersed in a solution on a surface of a substrate, or allowing the adsorbed metallic nanoparticles to be grown in a solution, thereby forming a film; applying infrared light to the substrate from the side thereof opposite to the side on which the metallic nano-thin film is disposed; detecting evanescent waves exuding from the substrate; and regulating a surface enhanced infrared adsorption activity while monitoring surface enhanced infrared adsorption signals in situ, whereby the metallic nano-thin film is grown in the form of flat and discontinuous islands.

An example where a silicon crystal of which the surface is coated with a native oxide film is used as the dielectric substrate and metallic nano-thin films of Au are adsorbed and disposed on the surface thereof is described in detail hereinunder. Here described is a case wherein an attenuated total reflectance-surface enhanced infrared absorption (ATR-SEIRA) method is used, an electroless plating method is used for film formation, and the characteristics of the film to be formed are "in-situ" monitored to produce a SEIRA sensor material. The evaluation method is a most rapid and direct SEIRA performance evaluation method for direct evaluation of optical characteristics in an infrared region.

As described in the above, the SEIRA activity increases with the reduction in the gap between the island-like metallic nano-thin films, and therefore, the film growth must be stopped just before percolation with a gap of a few nm or so kept remaining as such. For such accurate gap control, it seemingly appears that electronic diffraction or structure analysis with an electronic microscope or the like would be suitable. However, such structural analysis in fact takes a lot of time for measurement and data processing, and therefore could not be a monitoring method suitable for accurate gap control. As a method capable of instantaneously determining the timing for just-before stopping with real-time monitoring of growth and for attaining the intended object of the invention, utilized is an ATR-SEIRA method most suitable to "in-situ" monitoring in solution. Using the method, the material performance can be evaluated in a simplified manner and a high-sensitivity SEIRA sensor material can be realized with good reproducibility.

Figure 3:
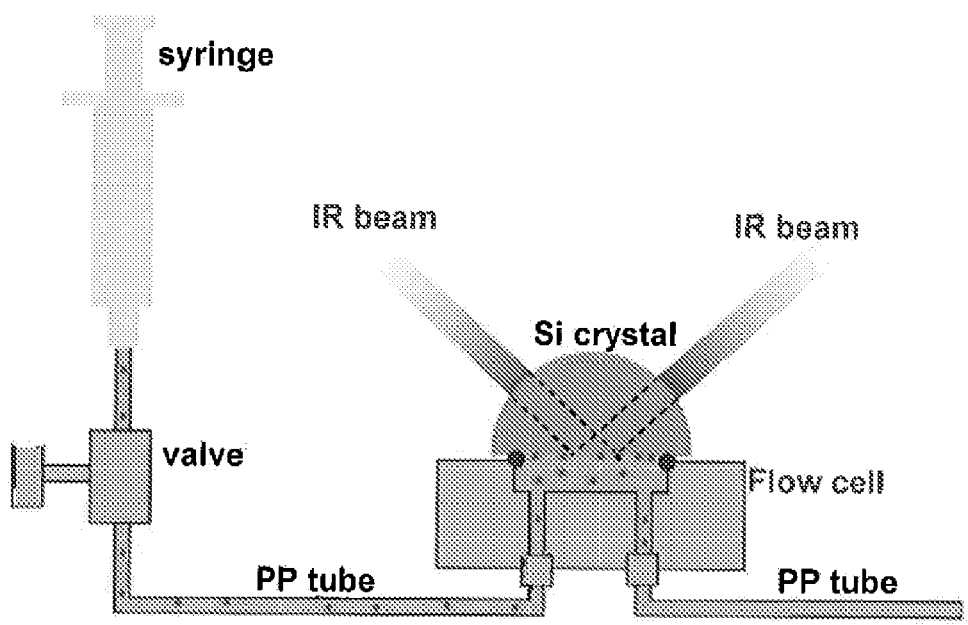
FIG. 3 is a schematic view of one example of a film-forming apparatus for use in the production method of the invention, which enables in-situ ATR-SEIRA measurement.
Figure 4:
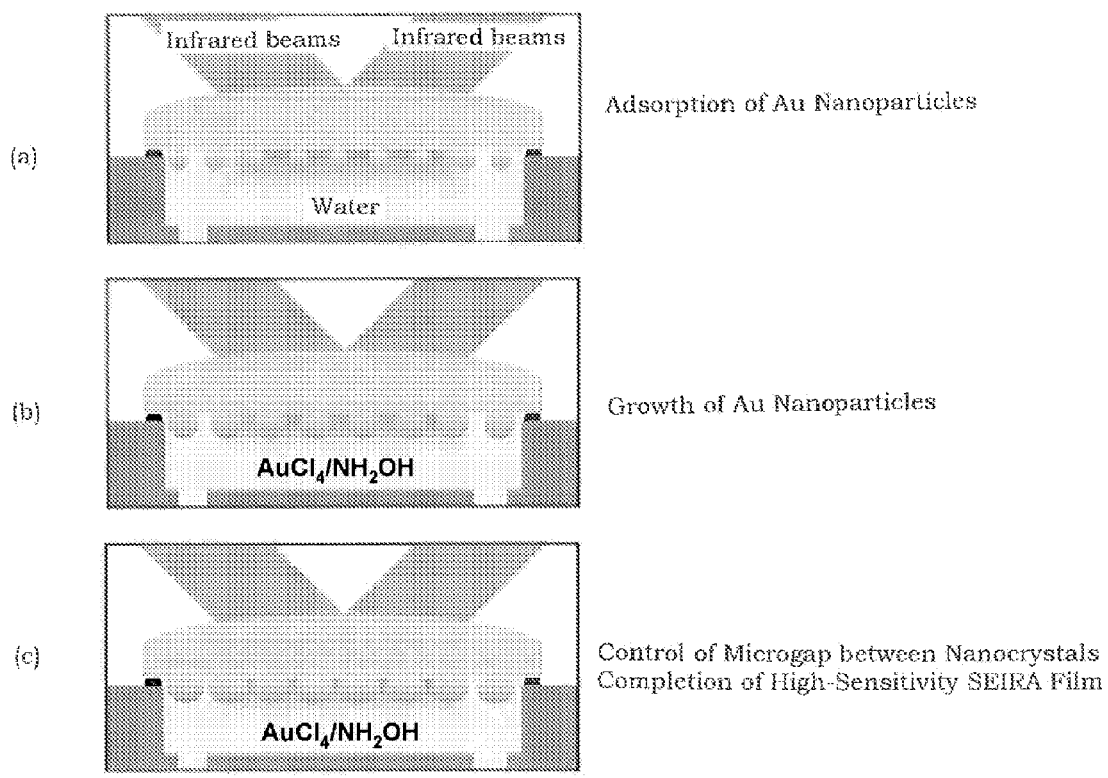
FIG. 4 is schematic views showing the appearance of the growth of a SEIRA sensor material.

FIG. 3 shows one example of a film-forming apparatus for use in the production method of the invention, which enables in-situ ATR-SEIRA measurement. FIG. 4 is schematic cross-sectional views showing the appearance of the growth of a SEIRA sensor material.

First, the surface of a silicon substrate of a semi-spherical Si-ATR crystal coated with a native oxide film is surface-modified with aminopropyltriethoxysilane (silane coupling agent). Next, as in FIG. 3, the silicon substrate is set on a flow cell, then an Au colloid solution (with heavy water) produced according to a citric acid reduction method is supplied to the flow cell through a syringe; and as shown in FIG. 4(*a*), the Au nanoparticles are adsorbed by the surface of the silicon substrate. Next, a growth solution is poured thereinto, and an Au film is grown from the adsorbed Au nanoparticles serving as growing nuclei, as shown in FIG. 4(*b*). For the growth, for example, used is $AuCl_4$/hydroxylamine. In the growth, infrared beams are radiated as shown in FIG. 4 for in-situ monitoring. When the monitored SEIRA sensitivity has reached the maximum, then the growth is stopped whereby a high-sensitivity SEIRA sensor material is formed as in FIG. 4(*c*).

Figure 5:
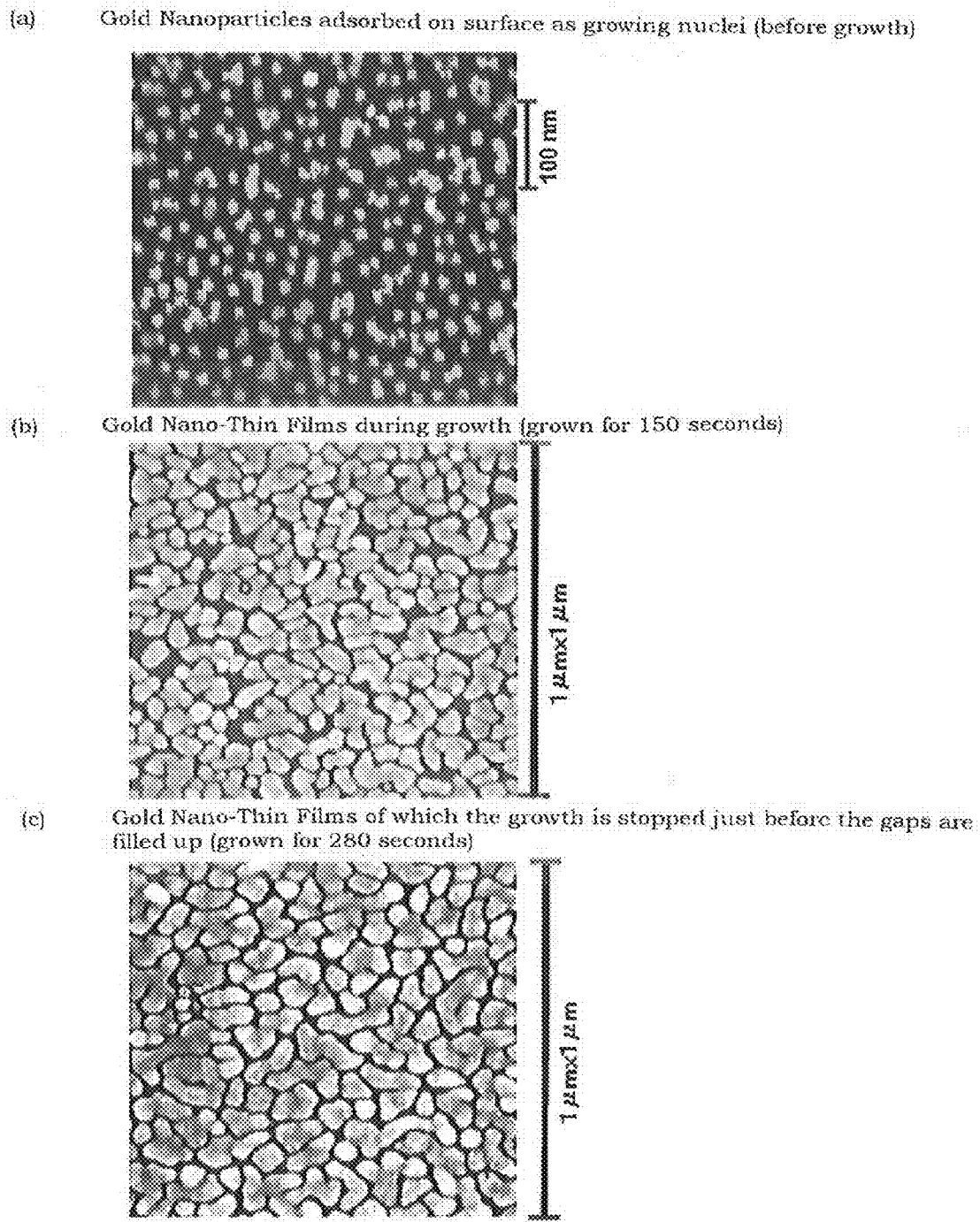
FIG. 5 includes scanning electron microscopic (SEM) images of a SEIRA sensor material in different growth stages.
Figure 6:
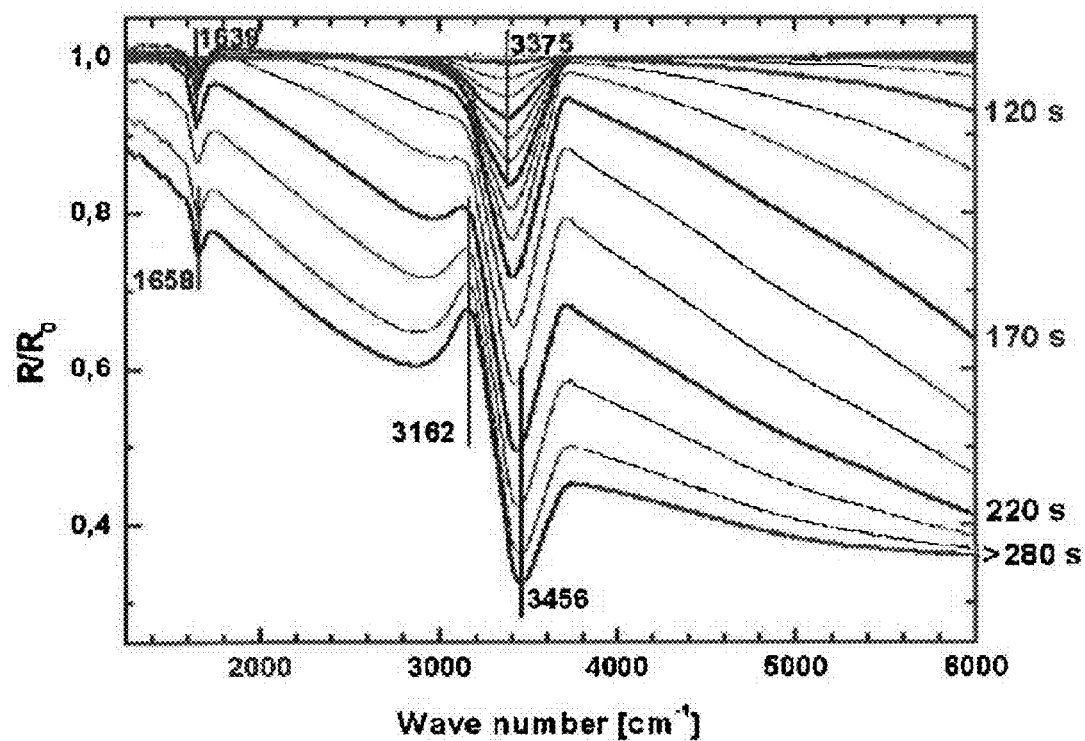
FIG. 6 is a view showing the time-dependent change of the spectrum of a SEIRA sensor material in in-situ ATR-SEIRA measurement.

FIG. 5 includes SEM images of the SEIRA sensor material in different growth stages. FIG. 6 shows the time-dependent change of the spectrum of the SEIRA sensor material in in-situ ATR-SEIRA measurement. In FIG. 6, the vertical axis indicates the relative reflectance; and $R_0$ of $R/R_0$ is the intensity of the reference spectrum of a fresh $D_2O$ that is in contact with the $SiO_2/Si$ interface.

Figure 7:
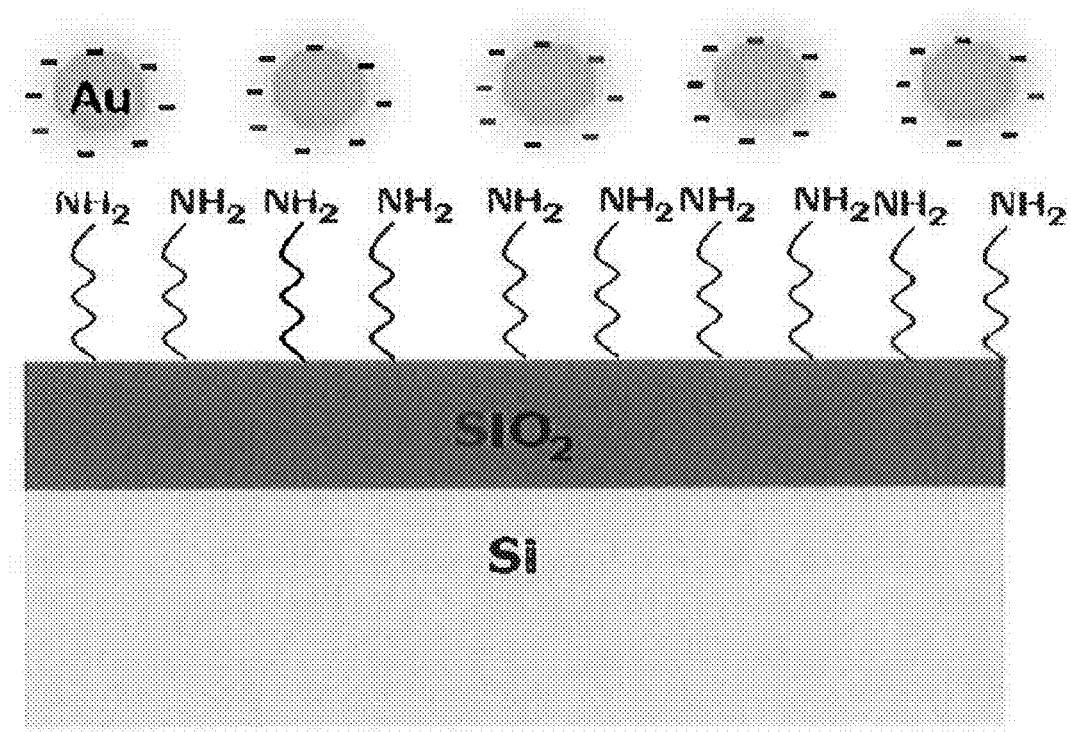
FIG. 7 is a schematic view of Au adsorption.

The principle is described. An electric field concentrates around the Au nanoparticles, and owing to the effect thereof, the absorption signal of molecular vibration around the particles may be enhanced up to from tens to hundreds times. Regarding the effect, it is said that the vibration signal from the molecules in from 2 to 3 molecular layers or so from the surface may be especially strongly detected. Here, using the effect, monitoring the adsorption dynamics of Au particles was tried. FIG. 7 shows a schematic view of Au adsorption. As the substrate, used was a silicon crystal coated with a native oxide film terminated with an amino group (surface treated with aminopropyltriethoxysilane). The Au nanoparticles (having an average diameter of 11 nm) were prepared by a citric acid reduction method. In this experiment, heavy water was used in place of water as the solvent, in which, therefore, overlapping of the O—H stretching vibration peak and the C—H peak to occur in a case where water is used can be prevented in the IR absorption spectrum, therefore facilitating quantitative analysis of the peaks. The IR beams were radiated from the lower side of FIG. 7 (from the Si side) under total reflectance (ATR) condition. Through irradiation with the IR beams, evanescent waves exuded from the interface to the solution. Based on the evanescent waves as a probe, the molecular vibration of the heavy water or citric acid molecule (OD or CH vibration) around the Au nanoparticles adsorbed by the interface is detected.

Figure 8:
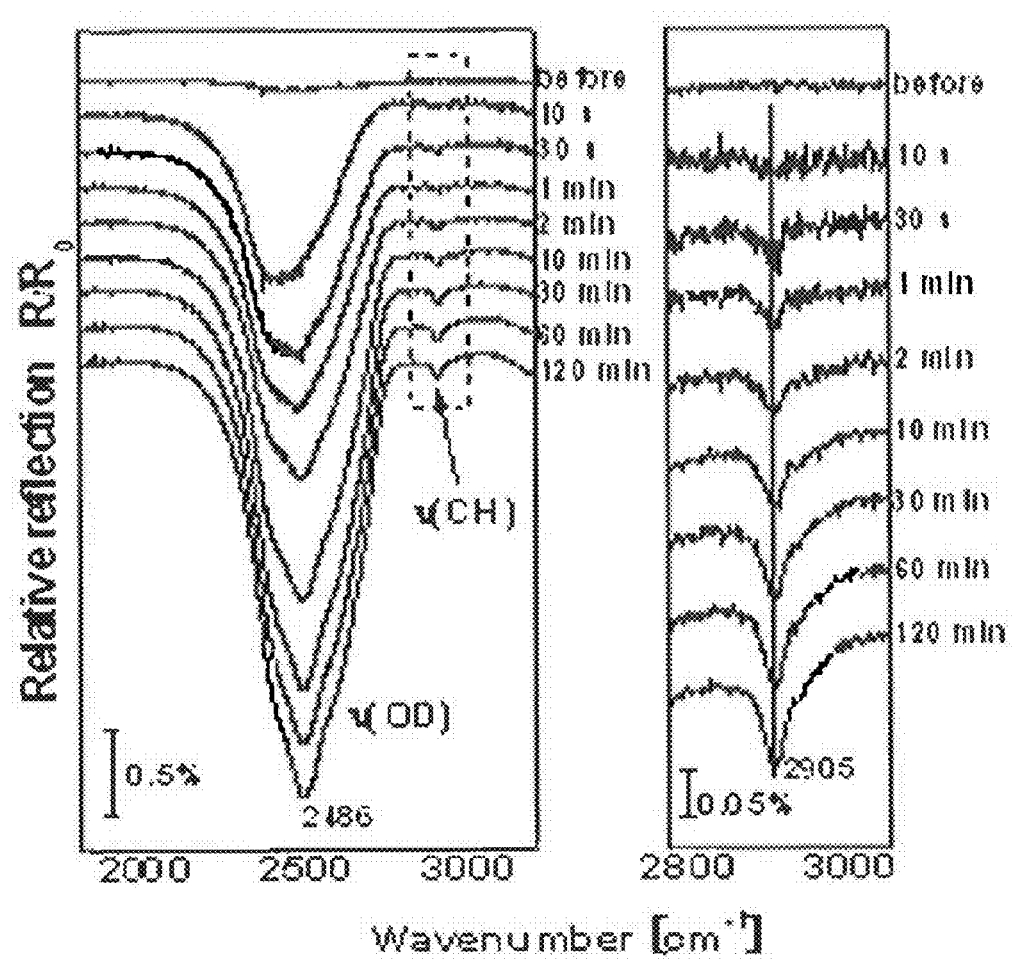
FIG. 8 is a graph showing the IR spectrum in a process of Au nanoparticle adsorption.

FIG. 8 is the IR spectrum in the process of Au nanoparticle adsorption. As shown in the left-side view, a broad and large absorption appears at 2486 cm$^{-1}$, and this is the OD stretching signal of heavy water that has been surface-enhanced by the SEIRA effect owing to the electric field concentration to the Au particles. The components of the absorption signals of the interface layer, the interlayer and the bulk are overlapped. The component of the interface at around 2400 cm$^{-1}$ decreased immediately after introduction of the colloid solution, and therefore, it is suggested that the condition of water in the interface has changed. The right-side view is an enlarged view of the part surrounded by the dotted line of the left-side view, in which the weak adsorption at 2905 cm$^{-1}$ is the CH stretching vibration signal derived from any of the underlayer surface-treating agent, aminopropyltriethoxysilane, or the citric acid molecule adsorbed by the Au particles around them during the production thereof. The intensity of the two signals of OD and CH increases immediately after exposure of the Au colloid solution to the silica surface, and is saturated in tens minutes.

Figure 9:
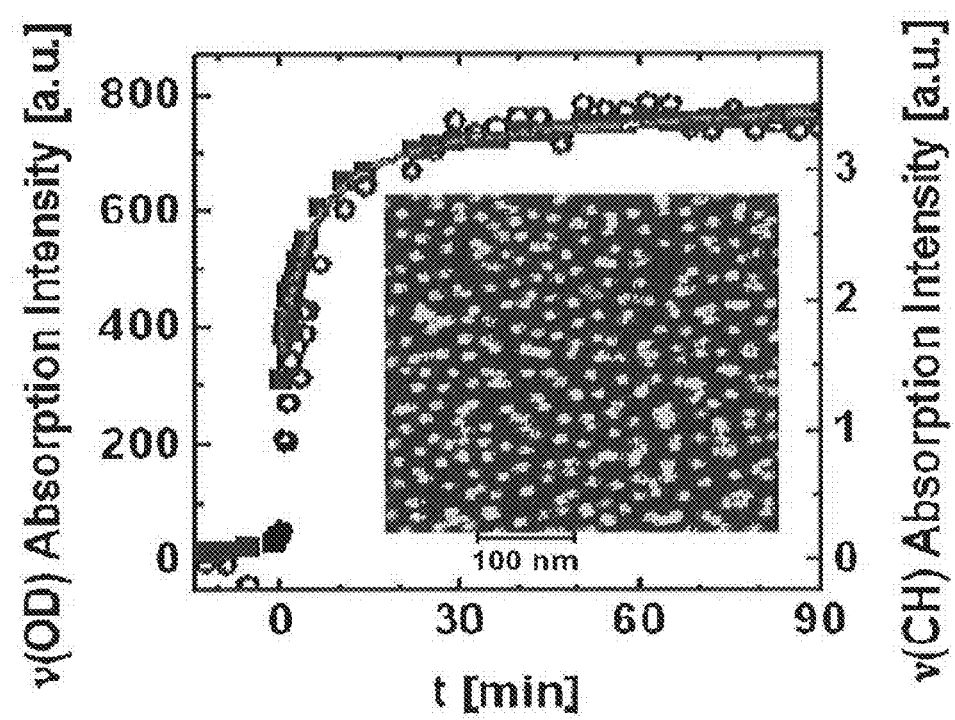
FIG. 9 is a graph drawn by plotting the data of OD and CH stretching vibration intensity relative to time.

FIG. 9 is a graph drawn by plotting the data of the OD and CH stretching vibration intensity relative to time. In the drawing, ■ is the data point of OD vibration intensity; and ○ is the data point of CH vibration intensity. The dipole strength of the CH vibration is small, and the absorption intensity thereof is smaller by 100 times than that of the OD vibration. In FIG. 9, however, the CH vibration intensity is completely synchronized with the OD vibration intensity, and it is obvious that the two follow the same kinetics. Since it is clear that the OD stretching vibration signal is derived from the Au particles, it is known that the CH stretching vibration detected here is not from the substrate base surface-treating agent but is a signal associated with the Au particles. In other words, the CH vibration observed here can be identified as the CH vibration from the citric acid that covers the Au particles.

From the time dependency of the vibration intensity, the adsorption kinetics of the Au nanoparticles can be discussed. The insert figure in FIG. 9 is, a scanning electromicroscopic (SEM) image of the Au nanoparticle film (beam energy, 10 kV). As known from this insert figure, the mean distance between the Au particles is substantially enough for their spacing from each other owing to the Coulomb repulsion (see FIG. 7) by the negative charge of citric acid, and it may be considered that the enhancing effect is mainly the electric field concentration effect around the individual particles (the dipolar field effect between the particles may contribute to it in some degree). The beam diameter of infrared light is around 1 mm or so, and the measured infrared absorption intensity is macroscopic average information, and therefore, it may be recognized that the measured data will be in proportional to the adsorption density of the Au particles.

The Au particles are charged negatively, and they bond to the base relatively strongly through coordinate bonding or electrostatic force. As a result, the adsorbed Au particles are fixed on the underlayer. Through SEM observation, it is considered that the Au particles are uniformly adsorbed and therefore the adsorption energy could be uniform throughout the entire region of the base surface. Further, when the adsorption in the first layer is completed, then the particles are not adsorbed by other two layers or more as observed in SEM because of the repulsion between the particles. As the most simplified model of adsorption of this case, there is known a Langmuir adsorption model; and it is interesting that as to whether or not the present case could follow such simple adsorption kinetics. Accordingly, using the following formula (1) for the time dependency of the coating rate of the case that follows the Langmuir adsorption model, fitting the experimental data in FIG. 9 thereinto was tried.

$$\theta(t) = 1 - e^{-ck_L t_\alpha} \tag{1}$$

It is known that, in this, when the value of the index $\alpha$ is 1, then the case is ordinary (gas adsorption or the like) Langmuir kinetics, and when $\alpha = \frac{1}{2}$, then the case corresponds to a diffusion-limited extended Langmuir model case. The gray curve in FIG. 9 is the result of best fitting, and surprisingly, the found data well correspond to the computed data. The experiment was repeated a few times, and the fitting parameter value obtained relative to the result was $ck_L = 0.134$, $\alpha = 0.39$ to 0.42. The value of $\alpha$ obtained herein is extremely near to the value of the extended Langmuir model. In other words, the rate at which the Au particles could reach the surface is limited by the Brownian motion of the Au particles in a solution. This indicates that the Au particles once having reached an interface and having been adsorbed by it are fixed thereon, and they block the adsorption of other particles by the same site. This is well understood in consideration of the fact that the Au nanoparticles are negatively-charged particles, as so mentioned above, and they act repulsively to each other between the particles owing to their repulsive force. The adsorbed particles dealt with herein are not ordinary atoms or molecules but are charged giantic complexes composed of tens of thousands of heavy metal atoms and coated with citric acid molecules. The adsorption sites are not specific sites, and as seen from the SEM pictures, they are adsorbed quite at random.

In this case and Example to be mentioned below, aminopropyltriethoxysilane is used as the linker molecule of the growth nuclei to the substrate; however, not limited to this, any other silane coupling agent such as aminopropyltrimethoxysilane, 3-phenylaminopropyltrimethoxysilane or the like is also usable.

In the above, a case with Au and a silicon substrate is described; and based on the same principle as above, other SEIRA sensor materials of the invention can also be produced using the above-mentioned materials and processing them under in-situ ATR-SEIRA monitoring.

In the above, an electroless plating method is used, but an electrolytic plating method may also be used.

Not limited to SEIRA sensors, the method is applicable also to any other electric field-enhanced sensors based on the effect of electric field concentration in gaps (hot-spot effect) or on the antenna resonance effect of metallic nanocrystals, and is expected to be applicable to fluorescent sensors or sensor materials based on surface enhanced Raman scattering.

Using the method, high-sensitivity SEIRA sensor materials can be produced and evaluated in a simplified manner, and the method is applicable to various chemical sensors and biosensors. For example, a SEIRA sensor film may be produced by growing it to the stage where percolation begins and gaps are partly filled up so as to increase the electric conductivity with lowering the sensitivity in some degree, and while it is used as a fuel cell electrode, the components in the electrode surface may be detected at high sensitivity to follow up the change of the electrode reaction.

EXAMPLES

The invention is described in more detail with reference to the following Examples.

As one example of the method of the invention, this Example is to demonstrate the formation of discontinuous Au nano-thin films grown on a silicon surface through electroless plating. First, a native oxide film-coated silicon single crystal for ATR was prepared, and this was coated with a silane coupling agent, (aminopropyl)triethoxysilane (abbreviated as APTES) for surface modification thereof.

Subsequently, the silicon single crystal was mounted on the liquid flow cell in FIG. 3, and an Au colloid solution prepared by a citric acid reduction method was poured into the flow cell.

The flow cell was constructed by combining a cell made of Teflon (trademark) and polypropylene (PP)-made tubes, fittings and valves; and a semi-spherical Si-ATR crystal was mounted on it. The Si-ATR and the flow cell were airtightly fixed to each other with a Kalrez (trademark) or Viton (trademark) O-ring to prevent solution leakage. In this Example, a single reflection ATR method was employed, but a cell for multi-reflection ATR may also be used.

The Au nanoparticles were adsorbed by the silane coupling agent on the silicon single crystal surface and fixed thereto, therefore forming a uniformly-adsorbed sub-monolayer Au nanoparticle film (see Non-Patent References 2 to 4). The fixation of the Au nanoparticles is by the strong attractive force between the amino group of the silane coupling agent and the Au nanoparticles (coordinate bonding, or Coulomb interaction). Near the once adsorbed Au nanoparticles, any additional Au nanoparticles are not subsequently adsorbed because of the Coulomb repulsive force between them; and therefore, the adsorption stops on the sub-monolayer level.

Subsequently, Au films were grown from the Au nanoparticles adsorbed by the silicon single crystal surface, serving as growing nuclei. For the growth, used was an $AuCl_4$/hydroxylamine solution. Before grown, the Au nanoparticle films were analyzed through ATR infrared absorption spectrometry for background determination.

Afterwards, the $AuCl_4$/hydroxylamine solution for growth was poured into the flow cell to start the growth of the Au nanoparticles. Based on the spectrum before pouring of the growth solution as a reference background spectrum, the absorption spectrum change relative to this was in-situ monitored whereby the film condition and the SEIRA activity were evaluated. The SEIRA activity was evaluated with monitoring the absorption peak of water. The OH stretching vibration peak of water profile showed a mountain peak at 3456 $cm^{-1}$ and was a valley peak at 31621 $cm^{-1}$, and it was confirmed that when the peaks in the vertical direction are substantially on the same level, the SEIRA sensitivity (signal enhancing degree) is the largest.

Figure 10:
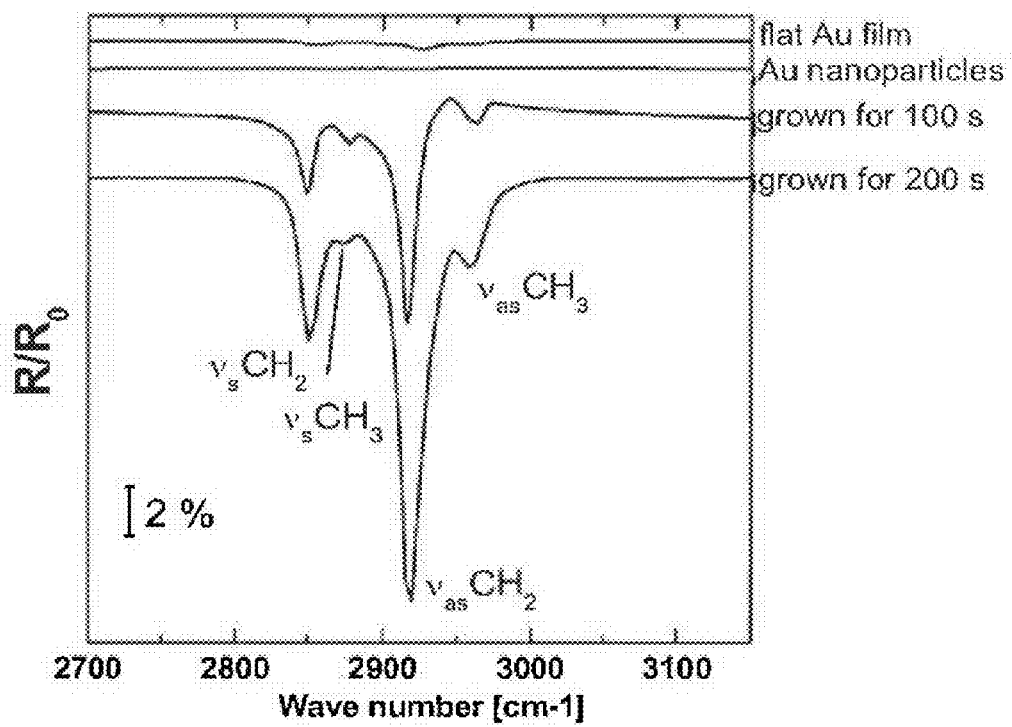
FIG. 10 is a view showing the performance comparison of formed sensor films (test results with octadecane-thiol).

The sensitivity was evaluated based on the CH stretching vibration peak intensity of octadecane-thiol (ODT) molecules stably adsorbed by the Au surface. The results are shown in FIG. 10. The film of which the SEIRA sensitivity reached the optimum was observed with a scanning microscope, and as a result, it was confirmed that the gap between the particles narrowed to a level of from a few nm to 20 nm or so. This is compatible with the fact that, when the gap is narrower, then the electric field concentration degree increases higher and the enhancing effect increases more.

It has been found that the SEIRA material prepared this time showed a higher intensity by at least 100 times as compared with a conventional completely flat film (measured according to a reflection method), and by at least 1000 times as compared with nanoparticles (measured according to an ATR method). In addition, the reproducibility of the SEIRA sensitivity of the produced film was high, and it has been verified that a high-performance sensor material can be produced in a simplified manner according to the present method.

Table 1 shows the test results with octadecane-thiol for performance comparison with the sensor film produced in the above-mentioned Example. There is a difference by 1000 times between the grown film and the ungrown nanoparticles (measured according to ATR method). The absorption intensity after growth was from 14 to 17%. In the experiment with dimethyl dithiocarbamate, the monomolecular adsorption showed an absorption intensity of 21%.

Figure 11:
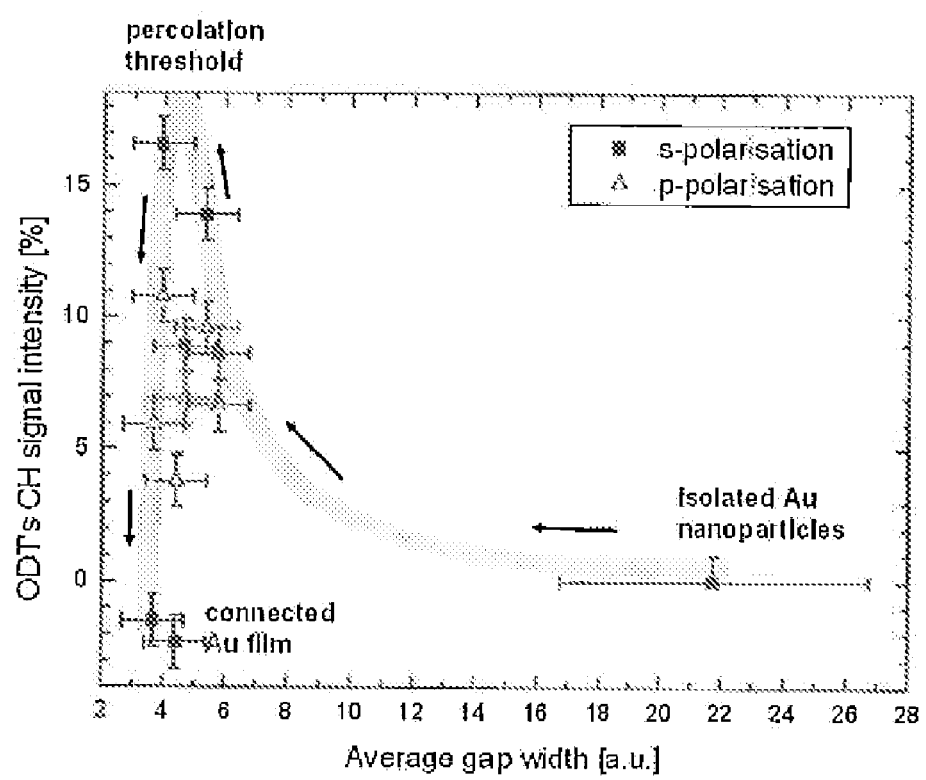
FIG. 11 is a view showing the relationship between the average gap width of grown gold nanoparticles and the infrared absorption intensity thereof.

The produced film was observed with a scanning electron microscope and, as a result, it has been found that, while growing flat, the nanoparticles kept the discontinuous state thereof though the gap between them was narrow. The average value of the nano-gaps was from 3 to 7 nm and was extremely small, and this means that the gap is narrowed and the electric field concentration effect is thereby enlarged to bring about a large infrared absorption intensity. The scanning microscopic observation results were analyzed and the relationship between the gap of the nanoparticles and the infrared absorption intensity was investigated, and the resulting data are shown in FIG. 11.

Figure 12:
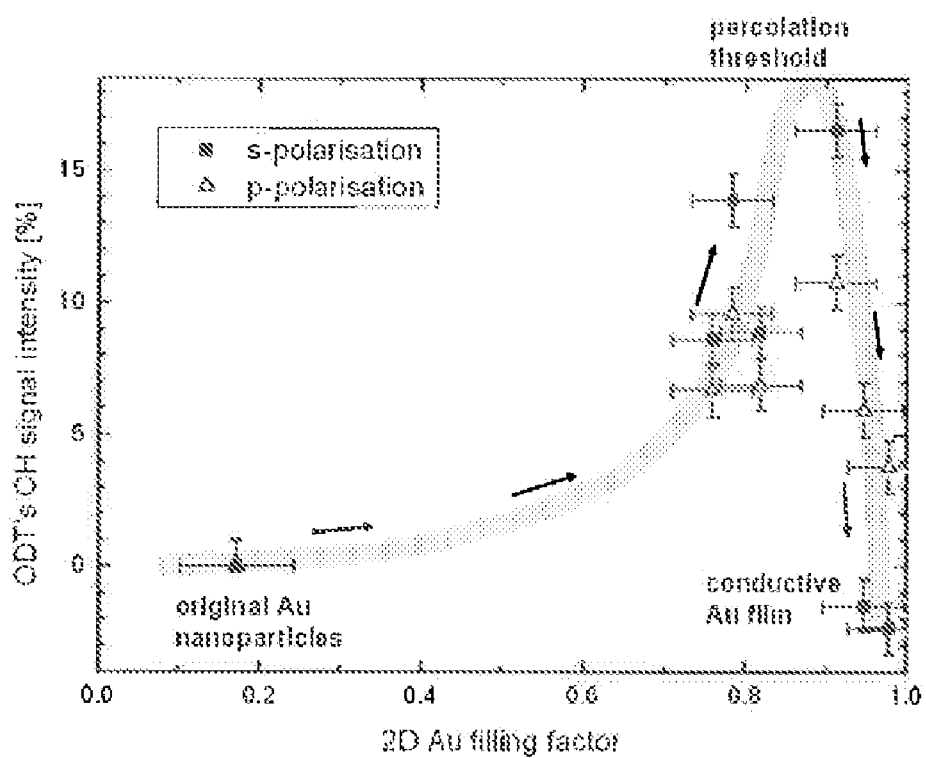
FIG. 12 is a view showing the intensity of the CH vibration infrared absorption of octadecane-thiol, as plotted relative to the two-dimensional filling rate of grown nanoparticles.

FIG. 12 shows the relationship between the two-dimensional filling factor and the absorption intensity of the film. The two-dimensional filling factor of the film exhibiting the highest enhancing effect was 0.83. In general, in a two-dimensional percolation model, the filling factor at which films begin to be connected together is 0.5; and as compared with this value, the result in this experiment shows an extremely large value. The high filling factor plays an important role for the activity of infrared absorption along with the small mean value of nano-gaps. In addition, the high filling factor naturally has a close relation to the small average value of gaps, and further, it is related to increasing the flatness of the film to thereby make the plasmon resonance frequency thereof shifted to an infrared region.

In summary, the present invention proposes the material satisfying the three points, 1) the films are not connected together in a range of at most 1 micron, 2) the average value of the gap between the grown nanoparticles is small (at most 7 nm), and 3) the nanoparticles have a high degree of flatness (the ratio of thickness-width of the nanoparticle is at most 0.2), as a material capable of realizing a high infrared absorption intensity.

The change in the infrared absorption intensity is extremely steep, and therefore, it is difficult to correctly determine the average gap value capable of giving a maximum enhancing degree, but it is known that the value could fall within a range of from 3 to 7 nm. When the average gap value is smaller than the range, then the films are connected together and the enhancing effect is greatly lowered. Anyone should be able to produce a film having an optimum enhancing effect based on the growth time thereof with good reproducibility; but in fact, in many cases, the time to be taken for producing an optimum film may fluctuate in a range of a few percent. In case where the formed films are connected together within the short period of time error of a few percent, then the infrared absorption activity suddenly lowers to the level before the growth. It is considered that heretofore this would be a bar to the production of high-performance sensor materials with good producibility. To solve the problem, it is necessary to stop the growth of the particles in a narrow state just before their connection together to such a degree that the gaps do not begin to be filled up. It is difficult to determine this in microscopic experiments, and it may be necessary to monitor the film condition in real time. For this, in the invention, while infrared light is applied in ATR configuration and the spectral profile of the growing film is monitored, the film growth is topped in optimum timing to thereby realize an infrared absorption sensor material having a high enhancing degree. As a result, in the invention, the inventors have found that the in-situ monitoring effect with infrared spectrometry is extremely effective for realizing the above-mentioned high-performance film. The method is a most correct and direct method, in which not the indirect information of the gap value, the filling factor and the like but the infrared absorption itself is monitored as the average information.

TABLE 1

Property of Au Film Grown for Different Time

| | Growth Time | | |
|---|---|---|---|
| | 0 second | 200 seconds | 210 seconds |
| CH Vibration Intensity of ODT (adsorption intensity in measurement by ATR method) | 0.03% | 16.6% | 13.8% |

Infrared Absorption Intensity of Molecular Vibration of Different Au Films Adsorbing Octadecane-thiol on the Surface

| | Type of Film | | | |
|---|---|---|---|---|
| | Flat Film (flat film on mica) | Nano-particle Film (not grown) | Grown Film (grown for 100 seconds) | Optimized Film (grown for 200 seconds) |
| CH Vibration Intensity of ODT | 0.3% (reflection method) | 0.04% | 8.6% | 16.6% |

INDUSTRIAL APPLICABILITY

The sensor material produced according to the method is applicable not only to a sensor material for infrared absorption spectrometry but also to that for fluorescent spectrometry, Raman scattering spectrometry, optical secondary harmonic wave generation or the like similarly based on electric field enhancement. Accordingly, the invention is applicable to chemical sensors, gas sensors, biosensors, and also to combinatorial chemistry and measurement equipment for medical diagnosis to which they are applied, and the ripple effects thereof to the related industry will be great.

The nano-thin film material to be formed on the dielectric substrate is not limited to metal alone, but may be applicable to any and every material capable of exhibiting an enhancing effect.

The invention claimed is:

1. A surface enhanced infrared absorption sensor material with a metallic nano-thin film adsorbed on a dielectric substrate, wherein the metallic nano-thin film is disposed on the substrate as flat and discontinuous islands having a two-dimensional filling factor from 0.7 to less than 1, the average gap between the adjacent islands is from 3 nm to 7 nm, and the degree of flatness, that is, the average value of the proportion of the thickness to the width of the island-like metallic nano-thin film is at most 0.2.

2. A method for producing a surface enhanced infrared absorption sensor with a metallic nano-thin film adsorbed on a dielectric substrate, characterized by:
   adsorbing metallic nanoparticles dispersed in a solution on a surface of a substrate;
   growing a film by using the adsorbed metallic nanoparticles as growing nuclei at the liquid solid interface in a solution;
   applying infrared light to the substrate from the side thereof opposite to the side on which the metallic nano-thin film is disposed;
   monitoring the reflected beam from the metal-substrate interface; and
   forming the metallic nano-thin film in the form of flat and disconnected islands by stopping the growth of the metallic nano-thin film at the growth stage when the surface enhanced infrared adsorption activity becomes maximum while monitoring surface enhanced infrared adsorption signals in situ, said metallic nano-thin film disposed on the substrate as flat and disconnected islands having a two-dimensional filling factor from 0.7 to less than 1, the average gap between the adjacent islands being from 3 nm to 7 nm, and the degree of flatness, that is, the proportion of the thickness to the width of the island-like metallic nano-thin film being at most 0.2.

3. The method for producing a surface enhanced infrared absorption sensor as claimed in claim 2, wherein the irradiation with infrared light is monitored according to an attenuated total reflectance method.

* * * * *